United States Patent [19]

Steinman et al.

[11] 3,978,224
[45] Aug. 31, 1976

[54] ANTIMICROBIAL HALO-SUBSTITUTED-2-CYANOETHYLAMINOALKYL-3-PHENYL-INDOLES

[75] Inventors: Martin Steinman, Livingston; Pirouz Tahbaz, Cedar Grove, both of N.J.

[73] Assignee: Schering Corporation, Kenilworth, N.J.

[22] Filed: July 1, 1975

[21] Appl. No.: 592,158

[52] U.S. Cl............................ 424/274; 260/326.15
[51] Int. Cl.². ............... C07D 209/14; A61K 31/40
[58] Field of Search................. 260/326.15; 424/274

[56] References Cited
UNITED STATES PATENTS
3,723,461  3/1973  Yamamoto et al. ........... 260/326.15

*Primary Examiner*—Lewis Gotts
*Assistant Examiner*—S. P. Williams
*Attorney, Agent, or Firm*—Bruce M. Eisen; Stephen B. Coan

[57] ABSTRACT

Disclosed are 2-cyanoethyl amino alkyl-3-phenyl indoles of the formula

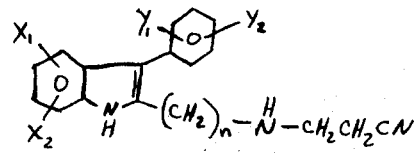

wherein $n$ 1, $X_2$, $Y_1$ and $Y_2$ are hydrogen or halogen, at least one of $X_1$ and $X_2$ being halogen; n is an integer selected from 1,2 and 3; and the acid addition salts thereof which are useful as antimicrobials.

9 Claims, No Drawings

ANTIMICROBIAL HALO-SUBSTITUTED-2-CYANOETHYLAMINOALKYL-3-PHENYL-INDOLES

This invention relates to antimicrobial compounds and compositions containing them, to a process for their preparation, and to their use as antimicrobial agents. "Antimicrobial" as used herein refers to antibacterial, antifungal and antiprotozoal activity.

The antimicrobial compounds of the invention are 2-cyanoethylaminoalkyl-3-phenylindoles of the formula I:

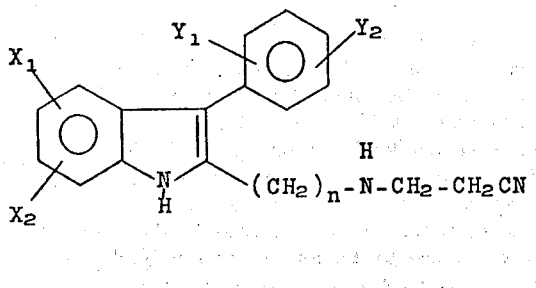

(I)

wherein $X_1$, $X_2$, $Y_1$ and $Y_2$ are hydrogen or halogen and at least one of $X_1$ and $X_2$ is halogen;

n is an integer selected from 1, 2 and 3.

The term "halogen" as used herein includes fluorine, chlorine, bromine and iodine. The preferred location of $X_1$, $X_2$, $Y_1$ and $Y_2$ is in the 5, 6, 2 and 4 position respectively. n is preferably one.

Particularly preferred compounds within the above formula are:

5-chloro-2-[N-(2-cyanoethyl)aminomethyl]-3-(2-fluorophenyl)indole
6-bromo-5-chloro-2-[N-(2-cyanoethyl)aminomethyl]-3-phenylindole
5-chloro-3-(2,4-dichlorophenyl)-2-[N-(2-cyanoethyl)aminomethyl]indole The acid addition salts can sometimes be used more conveniently than the indoles themselves; for example, because the the salts have more convenient physical properties such as crystalline form or solubility, or because the salts are more readily purified by recrystallization than the indoles. When the salts are used in food or medicine, the anion must, of course, be substantially non-toxic at the concentration or dosage used and may be a salt formed, for example, with one of maleic, phthalic, succinic, tartaric, citric, malic, cinnamic, sulphonic, hydrochloric, sulfuric and phosphoric acids. When the salts are used in technical fields such as the preservation of paper, leather or photographic goods, the anion need not necessarily by non-toxic.

The subject compounds can be prepared by cyanoethylation of the 2-aminoalkyl with acrylonitrile according to the reaction scheme:

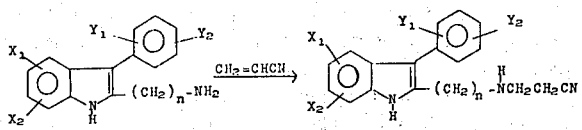

The following examples illustrate the preparation of cyanoethylaminoalkyl-3-phenylindoles of the present invention:

EXAMPLE 1

5-Chloro-2-[N(2-cyanoethyl)aminomethyl]-3-(2-fluorophenyl)indole hydrochloride

Treat 1.3 g of 2-aminomethyl-5-chloro-3-(2-fluorophenyl)indole with 8 ml of acrylonitrile and reflux for 16 hours. Concentrate to a residue and dissolve the residue in alcohol, e.g. ethanol. Add an ethanolic solution of hydrogen chloride, collect and dry the solid which precipitates out; the title compound melts at 212–213°C.

EXAMPLE 2

6-Bromo-5-chloro-2-[N(2-cyanoethyl)aminomethyl]-3-phenyl indole hydrochloride

Treat 2-aminomethyl-6-bromo-5-chloro-3-phenolindole with acrylonitrile in the same manner as in Example 1 to obtain the title compound which melts at 204°–205°C.

EXAMPLE 3

5-Chloro-3-(2,4-dichlorophenyl)-2-[N(2-cyanoethyl)aminomethyl]indole hydrochloride Treat 2-aminomethyl-5-chloro-3-(2,4-dichlorophenyl)indole with acrylonitrile in the same manner as in Example 1 to obtain the title compound which melts at 209°–210°C.

The following compounds may be prepared analogously in the same manner as in Examples 1 to 3.

6-bromo-5-chloro-2-[N(2-cyanoethyl)aminoethyl]-3-phenyl indole
5,7-dichloro-2-[N(2-cyanoethyl)aminoethyl]-3-(2,4-dichlorophenyl)indole
5,6-dichloro-2-[N(2-cyanoethyl)aminoethyl]-3-(2,4-dichlorophenyl)indole
5-chloro-2-[N-(2-cyanoethyl)aminoethyl]-3-(3,4-dichlorophenyl)indole
5-chloro-2-[N-(2-cyanoethyl)aminoethyl]-3-(2,4-dichlorophenyl)-5-fluoroindole
5-chloro-2-[N-(2-cyanoethyl)aminoethyl]-3-(2,4-dichlorophenyl)-6-iodoindole
5-chloro-2-[N-(2-cyanoethyl)aminoethyl]-3-(2-fluorophenyl)indole
5-chloro-2-[N-(2-cyanoethyl)aminoethyl]-3-(2,6-difluorophenyl)indole
6-chloro-2-[N-(2-cyanoethyl)aminoethyl]-3-(2,4-dichlorophenyl)indole
6-bromo-2[N-(2-cyanoethyl)aminoethyl]-3-phenylindole The compounds of formula I and their non-toxic acid addition salts can be used to treat diverse types of susceptible microbial infections. Furthermore, they are capable of preserving a wide variety of preparations including medical, veterinary, cosmetic and food preparations from microbial contamination; a stabilizing amount of such a compound is incorporated in the preparation in which the preservation is desired.

Susceptibility can be readily determined by standard in vivo and in vitro tests well known to the microbiologist. Genera of susceptible microorganisms include bacteria, fungi, and protozoa.

Exemplifying susceptible bacterial microorganisms are *Staphylococcus aureus, Streptococcus pyogenes C., Bacillus subtilis, Escherichia coli* and *Pseudomonas aeruginossa*. Susceptible fungi include *Candida albicans, Trichophyton mentagrophytes* and *Saccharomyces cerevisiae*. Susceptible protozoal pathogens include *Trychomonas vaginalis* and *Entamoeba histolytica*.

The invention therefore provides compositions containing, as an active ingredient, a 2-cyanoethylaminoalkyl-3-phenylindole of formula I or an acid addition salt thereof, in association with a suitable carrier, excipient or diluent. In its function as active ingredient the compound of the formula I or salt thereof may be used to preserve the carrier from microbial contamination; for example, the carrier may be cutting or other oil, paper, leather, photographic emulsion, canvas or rope. If the salt is non-toxic, the carrier may also be a food-stuff, food-additive or food-supplement, or a medicinal or cosmetic preparation. Such medicinal or cosmetic preparations may conveniently be in fluid form, e.g. lotions, creams, ointments, solutions, suspensions or aerosol preparations.

When used as preservatives, the compounds of the formula I or their salts are preferably incorporated into the composition to be preserved in an amount of 0.05 to 1% by weight, especially 0.1 to 0.5% by weight.

The compounds of formula I and their non-toxic acid addition salts can themselves be used in medicine as anti-microbial agents, and thus may be formulated as pharmaceutical compositions containing at least one said compound or salt together with a pharmaceutical carrier or excipient. Such a composition may, for example, be in the form of shaped products, in particular dosage units, such as pills, tablets, capsules, dragees, lozenges or suppositories (especially vaginal suppositories). Alternatively, such compositions may be adapted for injection and therefore have as carrier a sterile, pyrogen-free injectable liquid. Injectable compositions will normally be in the form of dosage units; the various dosage units mentioned conveniently contain from 2 to 100 mg., preferably from 5 to 50 mg., of a compound of formula I or non-toxic acid addition salt thereof.

Compositions for oral administration, other than dosage units mentioned above, may be exemplified by powders, granulates, solutions, suspensions, elixirs or aerosols. Compositions for topical application may be exemplified by ointments, creams, lotions, solutions, suspensions, aerosols, gels, shampoos, soaps or dusting powders. The composition when applied topically tend to show reduced dermal irritation compared to known antimicrobial compositions. The compositions may be adapted in particular as ophthalmic, otic and nasal preparations. Such compositions will normally be based upon standard carriers such as those selected from pharmaceutically acceptable vegetable oils, pharmaceutically acceptable polyalkylene glycols, isopropanol, gelatin, benzyl alcohol, gums, glycerol, petrolatum, preservatives starch, sugars such as lactose, talc, magnesium stearate, aerosol propellants such as chlorofluoroalkanes, and coloring, flavoring, sweetening, thickening, suspending, dispersing, emulsifying, wetting, stabilizing and buffering agents.

Compositions in which the active ingredient is a compound of the formula I or non-toxic acid addition salt thereof preferably contain from 0.5 to 10% thereof.

The following formulations exemplify pharmaceutical compositions containing 2-cyanoethylaminoalkyl-3-phenylindoles of this invention; the active ingredient illustrated may, of course, be replaced with another compound of formula I or nontoxic acid addition salt thereof.

Formulation 1

| Topical Cream | Per kg. |
|---|---|
| 5-chloro-2[N(2-cyanoethyl)aminoethyl]-3-(2-fluorophenyl)indole hydrochloride | 10 g.–100 g. |
| Ethoxylated Cetyl/Stearyl Alcohol | 20 g. |
| Cetyl Alcohol | 35 g. |
| Stearyl Alcohol | 35 g. |
| Petrolatum | 200 g. |
| Mineral Oil | 50 g. |
| Buffers, Sufficient | — |
| Preservatives, Sufficient | — |
| Purified Water to make | 1.0 kg. |

Add the cetyl alcohol, stearyl alcohol, ethoxylated cetyl/stearyl alcohol, petrolatum and mineral oil to a suitable mixing vessel. Heat to 80°C to melt. Mix. Add the preservatives, buffers and 5-chloro-2[N(2-cyanoethyl)aminoethyl]-3-(2-fluorophenyl)indole hydrochloride in approximately 95% of the purified water heated to 80°C in a suitable mixing vessel. Mix. Add the melted wax phase to the aqueous phase and mix while cooling to about 40°C. Add sufficient purified water to make 1 kg. Mix until cool.

Formulation 2

| Topical Ointment | Per kg. |
|---|---|
| 5-chloro-2-[N(2-cyanoethyl)aminoethyl]-3-(2-fluorophenyl)indole hydrochloride | 10 g.–100 g. |
| White Petrolatum, to make | 1.0 kg. |

Melt and heat the petrolatum to 50°C in a suitable mixing vessel. Remove a portion of the melted petrolatum and make therewith a slurry of the 5-chloro-2[N(2-cyanoethyl)aminoethyl]-3-(2-fluorophenyl)indole hydrochloride. Pass the slurry through a suitable colloid mill and mill until a uniform dispersion is obtained. Add the milled slurry to the remainder of the melted petrolatum and mix until cool.

We claim:

1. A compound of the formula:

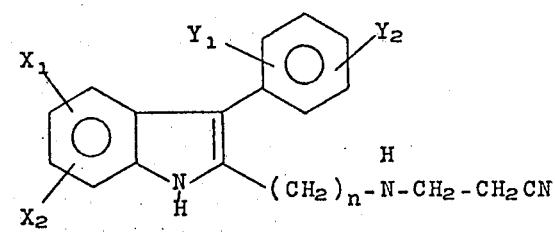

wherein $X_1$, $X_2$, $Y_1$ and $Y_2$ are hydrogen or halogen and at least one of $X_1$ and $X_2$ is halogen; n is an integer selected from 1, 2 and 3; and the acid addition salts thereof.

2. A compound of claim 1 wherein n is 1.

3. The compound of claim 1 which is 5-chloro-2-[N(2-cyanoethyl)aminomethyl]-3-(2-fluorophenyl)indole.

4. The compound of claim 1 which is 6-bromo-5-chloro-2-[N(2-cyanoethyl)aminomethyl]-3-phenylindole.

5. The compound of claim 1 which is 5-chloro-3-(2,4-dichlorophenyl)-2-[N(2-cyanoethyl)aminoethyl]indole.

6. A method for treating susceptible microbial infections, which comprises administering to an animal so infected an antimicrobially effective quantity of a compound of the formula:

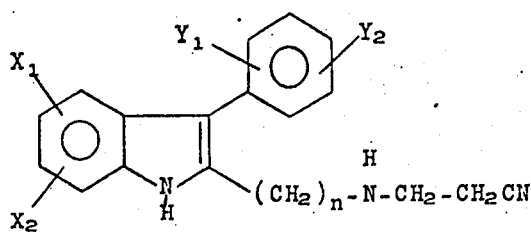

wherein $X_1$, $X_2$, $Y_1$ and $Y_2$ are hydrogen or halogen and at least one of $X_1$ and $X_2$ is halogen; and n is an integer selected from 1, 2 and 3; and the acid addition salts thereof.

7. The method of claim 6 wherein the compound is 5-chloro-2-[N-(2-cyanoethyl)aminomethyl]-3-(2-fluorophenyl)indole.

8. The method of claim 6 wherein the compound is 6-bromo-5-chloro-2-[N(2-cyanoethyl)aminomethyl]-3-phenyl indole.

9. The method of claim 6 wherein the compound is 5-chloro-3-(2,4-dichlorophenyl)-2-[N(2-cyanoethyl)aminomethyl]indole.

* * * * *